United States Patent [19]
Zimmermann et al.

[11] Patent Number: 6,090,793
[45] Date of Patent: Jul. 18, 2000

[54] NON-MITOGENIC SUBSTANCE, ITS PREPARATION AND USE

[75] Inventors: Ulrich Zimmermann, Waldbrunn; Konrad Federlin; Tobias Zekorn, both of Giessen; Gerd Klock, Zell am Main, all of Germany

[73] Assignee: Monsanto Europe S.A., Brussels, Belgium

[21] Appl. No.: 08/284,581

[22] PCT Filed: Feb. 12, 1993

[86] PCT No.: PCT/DE93/00136

§ 371 Date: Aug. 10, 1994

§ 102(e) Date: Aug. 10, 1994

[87] PCT Pub. No.: WO93/16111

PCT Pub. Date: Aug. 19, 1993

[30] Foreign Application Priority Data

Feb. 12, 1992 [DE] Germany .............................. 42 04 012

[51] Int. Cl.[7] .............................. A23L 1/05; C08B 37/04; A61L 15/00; A01N 43/04
[52] U.S. Cl. .................................. 514/54; 514/23; 536/3; 536/123.1; 424/93.7; 424/445; 435/101; 435/174; 435/178; 435/180; 435/240.22; 435/182; 426/573
[58] Field of Search .................................. 424/93.7, 445; 435/101, 174, 178, 182, 240.22, 180; 514/54, 23; 536/3, 123.1; 426/23

[56] References Cited

U.S. PATENT DOCUMENTS

| | | | |
|---|---|---|---|
| 4,235,966 | 11/1980 | Jarman et al. | 435/101 |
| 4,578,458 | 3/1986 | Pier | 435/101 |
| 4,869,902 | 9/1989 | Buehler et al. | 424/686 |
| 4,933,185 | 6/1990 | Wheatley et al. | 424/94.3 |
| 5,166,137 | 11/1992 | Otterlei et al. | 514/23 |
| 5,459,054 | 10/1995 | Skjak-Braek et al. | 435/178 |

OTHER PUBLICATIONS

Journal of Chromatography, 89 (1974) 99–102 Polyacrylamide gel electrophoresis of alginic acid—C. Bucke.

Electrohoresis 1992, 13, 269–274, Zimmerman et al., Production of mitogen–contamination free alginates with variable ratios of mannuronic acid to guluronic acid by free flow electrophoresis.

*Primary Examiner*—Herbert J. Lilling
*Attorney, Agent, or Firm*—Fitzpatrick, Cella, Harper & Scinto

[57] ABSTRACT

Proposed is a mitogen-free substance comprising crosslinked copolymers including 10 to 90 mole % of guluronic acid, the balance being made up of mannuronic acid. The substance has a molecular weight of from 10,000 to 500,000 Daltons. Also proposed are methods for preparing such substances and their use.

15 Claims, No Drawings

NON-MITOGENIC SUBSTANCE, ITS PREPARATION AND USE

The invention relates to a non-mitogenic substance using guluronic acid or mannuronic acid, its preparation and use.

According to standard terminology, the term mitogenic defines those substances that stimulate the division of cells which would otherwise (i.e., without the influence of this substance) not divide. The reactions thereby triggered in the organism are abnormal and may manifest as allergic, immunologic and pyrogenic (inflammatory) reactions. It requires no further explanation that the development and production of non-mitogenic substances are of the greatest interest for the contact with living organisms in biology and medicine.

In the area of implant surgery, the application of non-mitogenic substances is of the greatest importance in order to suppress immunologic reactions that would otherwise be induced causing a rejection of the implant. In the treatment of numerous illnesses, living cells are introduced into the organism which, on the one hand, are supplied with nutrients and, on the other hand, compensate for an underproduction or complete failure of intrinsic cells by producing cell secretions, hormones, etc., according to the individual requirements.

One of the best known illnesses of this type is diabetes. Although the deficiency of insulin can be adjusted by well-dosed exogenous administration in timed intervals, it should be noted that an exact 24-h dosage in the sense of a regulating mechanism can never be achieved, so that fluctuations and deviations from the ideal level are inevitable. This disadvantage can be corrected by implanting living cells into the organism. In order to suppress immunologic reactions, however, the cells must be placed in capsules which, in turn, must meet the following requirements: uninhibited diffusion through the walls to permit the supply with nutrients on the one hand, and the release of the cell secretions, hormones, etc. on the other hand, must be ensured. In addition, it must be ensured that the implant does not cause immunologic reactions (i.e., it must be non-mitogenic), which would manifest in a fibrotic growth on the capsule surface after a certain period of time, obstructing the required circulation and exchange of nutrients and cell secretions.

The objective of this invention is the development, preparation and application of a non-mitogenic substance which does not cause allergic, immunologic and pyrogenic reactions, even after prolonged contact with the living organism.

According to the invention, this objective is met with copolymers of a molecular weight between 10,000 and 500,000 dalton, which consist of 10 to 90 mol % of guluronic acid, each supplemented to 100% with mannuronic acid.

The only component of the non-mitogenic substance may be a copolymer of guluronic acid and mannuronic acid with a molecular composition of 10 to 90 mol % of guluronic acid and the remainder being mannuronic acid. Because of the given molar ratio of both acids, the size of the copolymer that is formed during polymerization has not been determined. Consequently, copolymers with a low molecular weight which do not meet the requirements can also be identified. Therefore, an additional requirement is a molecular weight of the copolymer between 10,000 and 500,000 dalton. Such molecular weights are relatively easy to obtain by dialysis using membranes and filters with suitable permeability and pore radius.

Non-mitogenicity is determined by testing the substance that was polymerized with calcium for in vitro induction of measurable proliferation of spleen lymphocytes. For this purpose, splenocytes are collected from mice of the inbred strain Balb-c. Cells at a count of $1 \cdot 10^6$ ml$^{-1}$ were cultivated at 37° C. in the presence of 100 $\mu$g ml$^{-1}$ of the mitogenic substance in the following growth medium: RPMI 1640 medium, 10% fetal bovine serum (Boehringer, Mannheim, Germany), 2 mM L-glutamine, 2 mM sodium pyruvate, non-essential amino acid (1x, Boehringer, Mannheim, Germany), 50 $\mu$M 2-mercaptoethanol, 100 units ml$^{-1}$ of penicillin and 100 $\mu$g ml$^{-1}$ of streptomycin (Biochrom, Berlin, Germany). The lymphocytes showed neither a significant incorporation of $^{14}$C or $^3$H thymidine into acid precipitable cellular substances (measured after 3 days) nor microscopically detectable growth (microscopic cell count after 5 to 9 days of cultivation).

In the scope of the invention, the admixture of other, in view of mitogenicity, safe components in addition to the described copolymer is basically optional.

Non-mitogenicity of the substance does not necessarily equal biocompatibility in vivo. This property rather depends on other factors, such as the surface characteristics of the implant and the location of the implantation. Nevertheless, it is beneficial to choose compounds that are found to be biocompatible. Biocompatibility with regard to the induction of foreign body reactions is tested in animal experiments using mice and rats. In the specific conduct of the experiment, capsules of substances that were polymerized with barium or calcium were prepared and implanted in the peritoneum of these animals. Neither fibrotic growth nor foreign body reactions were observed in the surrounding tissue. In the specific case, a 2% solution of the substance was polymerized with 20 mM $BaCl_2$ in 0.9% NaCl, whereby gel pellets of 0.5 to 1 mm diameter were formed. These were washed with 0.9% NaCl, incubated for two days in RPMI 1640 medium and implanted in the peritoneum of mice and rats. After three weeks, the capsules were retrieved by peritoneal lavage and histologically analyzed.

An additional characteristic of the non-mitogenic substance is employed by the electrophoretic mobility and is described as follows: the substance consists of a component formed as a copolymer of 10 to 90 mol % of guluronic acid, with the remainder, i.e. 90% to 10%, being mannuronic acid. The potential copolymers defined by this chemical composition may be very different with regard to molecular size and the respective molecular configuration. In order to extract the non-mitogenic substance, the different copolymers are subjected to carrier-free electrophoresis in which the fractions of interest show a mobility between 3 and $5 \cdot 10^{-4}$ cm$^2 \cdot$V$^{-1} \cdot$s$^{-1}$. Specific experiments in this context were conducted in a 30·130·0.3 mm separation chamber, at a chamber buffer temperature of 22° C., a chamber buffer composition of 15 mM triethanolamine, 7.1 mM potassium acetate, 216 mM glycine (pH 7.2), 11 mM glucose, 0.2 mM ethylenediamine tetraacetate, 100 units ml$^{-1}$ of penicillin, 100 $\mu$g·ml$^{-1}$ of streptomycin, at a conductivity of 1.9 mS cm$^{-1}$. The buffer was pumped through the chamber at a speed of 2.5 ml·h$^{-1}$. The pump was injected at a rate of 350 $\mu$l·h$^{-1}$. The field intensity was 100 V·cm$^{-1}$ (the electric current was 65 mA). As an additional requirement, the substance must have a molecular weight between 10,000 and 500,000 dalton. Copolymers of these molecular weights can be separated by diffusion through a membrane.

The inventive merit of the suggested substance is revealed in the fact that, with reference to specific experiences and experiments, experts believe that mannuronic acid as a substance in itself and copolymers containing mannuronic acid were mitogenic (see Journal of Immunotherapy 10, pp. 286–291, 1991, Raven Press, New York; Transplantation Proceedings Vol. 23, No. 1 (February) 1991, pp. 758–759). The merit of this invention is the discovery of the inaccuracy of the above claim. In addition to that, alginates generally demonstrate mitogenic reactions which are—and this is another important discovery—to be attributed to inevitable environmental pollution due to their derivation and extraction from natural products.

Substances that are characterized by non-mitogenic properties can be derived from raw alginates by specified production procedures.

Described below are two procedures for the preparation of the previously cited non-mitogenic substances. The first uses carrier-free electrophoretic processes, while in the second procedure, the substance is obtained by chemical reaction. Common to both procedures is the starting material of alginate which is extracted from plants, algae, bacteria, etc., and which is commercially available.

An up to 10% alginate solution is introduced into an electrophoresis buffer with an electric conductivity of 2 mS·cm$^{-1}$, followed by separation into fractions of different electrophoretic mobility, which are collected separately. The electrophoretic mobility of interest is between 3 and 5·10$^{-4}$ cm$^2$·V$^{-1}$·s$^{-1}$. Subsequently, separation according to diffusibility which differs by molecular weight, is conducted by additional dialysis against water. The non-mitogenic substance is obtained by collection of molecular weights between 10,000 and 500,000 dalton from the entire copolymer.

A chemically based production procedure is described below, in which the alginate extracted from plants, algae, bacteria, etc., was initially cross-linked into an insoluble complex that allows washing and extraction as well as subsequent recovery. In this procedure, the alginates are precipitated by addition of Ba$^{++}$ ions or similar multivalent ions (lead Pb, copper Cu) with a similar or higher affinity for alginate than barium, followed by extraction with an acid, such as acetic acid, over several hours at increased temperatures. After washing, further extractions are conducted in an alkaline range using complex forming agents, such as citric acid. After washing in distilled water, the gel pellets are stirred for several hours in an alcohol, such as ethanol. The washed, but still cross-linked alginates are released by addition of EDTA (ethylenediamine tetraacetic acid) in a highly alkaline range. The gel pellets dissolve in this process. The result is a non-mitogenic substance derived from raw alginate.

Following is a detailed description of a chemically based production process:

A 2 to 4% solution of raw alginate is filtered through a membrane filter of 0.22 μm pore size and subsequently drop-added under agitation into a 5-fold volume of a 50 mM barium chloride solution, whereby gel pellets of 1 to 5 mm in diameter are formed. After 10 to 20 minutes, the gel pellets are washed in distilled water and subsequently stirred twice for 3 to 4 hours at 60 to 80° C. in 1 L each of 1M acetic acid/10 mM BaCl$_2$. The gel pellets are then washed on a sieve with distilled water and stirred overnight in 2×1 L of 50 mM citric acid (pH-value 8.0 with KOH), with a medium change after 4 hours. The gel pellets are re-washed in distilled water and are subsequently stirred for 2 to 3 hours in 500 ml of 80% ethanol for 1 hour each in 1 to 2 hours in distilled water. [sic.]The gel pellets are decanted through a sieve and suspended in 200 ml of a 250 mM EDTA solution (pH 10.0 with KOH). After overnight stirring the pellets dissolved. The solution is dialyzed 3× against distilled water (pH 8.5 with KOH) for at least 4 hours and subsequently freeze-dried.

Following are some examples of applications for the non-mitogenic substance as described according to the invention. They have in common that they are accepted by the animal or human body without problems and safely prevent the induction of mitogenic reactions, even after long-term use.

First, the area of transplant surgery should be mentioned, in which non-mitogenic substances can be used for the encapsulation and implantation of living cells without inducing immunologic reactions by the human body. A particularly important example is the enclosure of insulin-generating cells (islets) in capsules of non-mitogenic substances which do not tend to develop fibrotic growth, even after long-term implantation, as was proven in animal experiments. The capsule permits the diffusion of nutrients necessary for the maintenance of cell growth as well as the excretion of hormones—in the case of diabetes, this would be insulin—that are produced in this process. This application simultaneously employs the permeability for glucose, oxygen, peptide hormones—insulin is classified as such—as well as the impermeability for larger molecules, such as in antibodies. The implantation of living cells (islets of Langerhans) permits an ideal adjustment of the immediate hormone demand in the sense of a regulating mechanism.

Further, non-mitogenic substances are particularly suited for use as a food additive, where they are known to aid gelling and stabilization. Statistical studies suggest connections between the use of (the current) alginates and the incidence in the development of gastrointestinal tract cancer. These currently used alginates are polluted and therefore—as established by the invention—mitogenic. Substitution with non-mitogenic alginates would have significant health benefits.

Finally, non-mitogenic substances can be used externally for closing wounds from injuries as well as internally for ulcers, particularly stomach ulcers. They can be safely used as dental impression compounds and, in capsule or pellet form, serve in galenic medicine as pharmaceutical carrier substances which dissolve in the stomach or intestine, releasing the encapsulated pharmaceutical compound. In the same manner, it can be used as a vehicle for contrast media in which, for example, air bubbles are absorbed and encapsulated, which serves contrasting in ultrasonic scans.

What is claimed is:

1. A non-mitogenic substance comprising guluronic and mannuronic acid, in which the substance comprises copolymers consisting of about 10 to 90 mol % of guluronic acid and about 90 to 10 mol % of mannuronic acid and in which the copolymers have a molecular weight of about 10,000 to 500,000 daltons and an electrophoretic mobility between about 3 and 5·10$^{-4}$ cm$^2$·V$^{-1}$·s$^{-1}$.

2. The non-mitogenic substance according to claim 1, wherein the substance is biocompatible.

3. A method for implanting living cells in a patient which comprises encapsulating the living cells with the non-mitogenic substance of claim 1 to form encapsulated living cells, and introducing the encapsulated living cells into the patient.

4. A method for stabilizing a food which comprises adding the non-mitogenic substance of claim 1 to the food.

5. A method for gelling a food which comprises adding the non-mitogenic substance of claim 1 to the food.

6. A method for treating an internal or external wound which comprises applying the non-mitogenic substance of claim 1 to the wound.

7. A method for making a dental impression of a dental formation which comprises applying the non-mitogenic substance of claim 1 to the formation.

8. A method for administering a pharmaceutical to a patient which comprises combining the pharmaceutical with the non-mitogenic substance of claim 1 to form a non-mitogenic pharmaceutical composition, and introducing the composition into the patient.

9. A method for the preparation of the non-mitogenic substance of claim 1, comprising the steps of:

(i) fractionating an alginate solution of up to 10% alginate by carrier-free electrophoresis to provide a fraction having an electrophoretic mobility between 3 and $5 \cdot 10^{-4}$ cm$^2 \cdot$V$^{-1} \cdot$s$^{-1}$;

(ii) dialyzing said fraction; and, (iii) separating alginate with a weight between 10,000 and 500,000 daltons from said dialyzed fraction to recover the non-mitogenic substance.

10. A method for the preparation of the non-mitogenic substance of claim 1, comprising the steps of:

(i) precipitating from an alginate solution an insoluble alginate complex;

(ii) extracting said alginate complex with an acid;

(iv) extracting said alginate complex with a complex forming agent;

(vi) treating said alginate complex with an alcohol;

(vii) treating said alginate complex with EDTA; and, (vii) recovering the non-mitogenic substance.

11. The method according to claim 10, wherein the alginate complex is precipitated by the addition of Ba$^{++}$ ions.

12. The method according to claim 10, wherein the alginate complex is precipitated by the addition of multivalent cations.

13. The method according to claim 10, wherein the complex forming agent is citric acid.

14. The method according to claim 10, wherein the steps of extracting with a complex forming agent and the step of treating with EDTA is conducted at an alkaline pH.

15. The method according to claim 10, wherein the alginate solution is obtained by extraction of plants, algae or bacteria.

* * * * *

UNITED STATES PATENT AND TRADEMARK OFFICE
CERTIFICATE OF CORRECTION

PATENT NO. : 6,090,793

DATED : July 18, 2000

INVENTOR(S) : ULRICH ZIMMERMANN ET AL.

It is certified that error appears in the above-identified patent and that said Letters Patent is hereby corrected as shown below:

COVER PAGE:

At [56] under "OTHER PUBLICATIONS", "Electrohoresis" should read --Electrophoresis--.

COLUMN 6:

Line 16, "is" should read --are--.

Signed and Sealed this

Twenty-second Day of May, 2001

*Attest:*

NICHOLAS P. GODICI

*Attesting Officer*     *Acting Director of the United States Patent and Trademark Office*